(12) United States Patent
Tsuruoka et al.

(10) Patent No.: US 6,790,381 B2
(45) Date of Patent: Sep. 14, 2004

(54) DRYING AGENT

(75) Inventors: Yoshihisa Tsuruoka, Mobara (JP); Hisamitsu Takahashi, Mobara (JP); Satoshi Tanaka, Mobara (JP); Shigeru Hieda, Mobara (JP)

(73) Assignee: Futaba Corporation, Chiba-ken (JP)

( * ) Notice: Subject to any disclaimer, the term of this patent is extended or adjusted under 35 U.S.C. 154(b) by 0 days.

(21) Appl. No.: 10/288,665

(22) Filed: Nov. 5, 2002

(65) Prior Publication Data

US 2003/0110981 A1 Jun. 19, 2003

(30) Foreign Application Priority Data

Nov. 7, 2001 (JP) ........................................ 2001-341308

(51) Int. Cl.[7] .............................. C09K 3/00; C07F 5/06
(52) U.S. Cl. ........................ 252/194; 556/40; 556/175; 106/287.17; 106/287.18
(58) Field of Search ..................... 252/194; 106/287.17, 106/287.18; 556/40, 175

(56) References Cited

U.S. PATENT DOCUMENTS

| | | | |
|---|---|---|---|
| 3,730,914 A | * 5/1973 | Dowd ............................ | 528/9 |
| 3,856,839 A | * 12/1974 | Smith et al. ................... | 556/40 |
| 4,312,769 A | * 1/1982 | Pratt ............................ | 508/505 |
| 4,560,716 A | 12/1985 | Sato et al. ................... | 523/451 |
| 5,268,145 A | 12/1993 | Namba et al. ................. | 422/57 |
| 6,111,357 A | 8/2000 | Fleming et al. ............. | 313/509 |
| 6,656,609 B2 | * 12/2003 | Takahashi et al. .......... | 428/690 |
| 2002/0015818 A1 | 2/2002 | Takahashi et al. ............ | 428/76 |

FOREIGN PATENT DOCUMENTS

| | | |
|---|---|---|
| EP | 0 114 258 A1 | 8/1984 |
| GB | 2368192 A | 4/2002 |
| HU | 39709 | 10/1986 |
| JP | 59-099782 | 6/1984 |
| JP | 61-160981 | 7/1986 |
| JP | 04132778 | 5/1992 |
| JP | 04-249590 | 9/1992 |
| JP | 04-255693 | 9/1992 |
| JP | 07062279 | 3/1995 |
| JP | 60-224250 | 11/1995 |
| JP | 2000-324407 | 4/2000 |
| WO | WO 94/07344 | 3/1994 |

OTHER PUBLICATIONS

Chemical Abstracts, Abstract No. 117:173516 corresponding to JP 04132778 (May 7, 1992).
Chemical Abstracts, Abstract No. 123:146871 corresponding to JP 07062279 (Mar. 7, 1995).
Chemical Abtracts, Abstract No. 108:23685 corresponding to HU 39709 (Oct. 29, 1986).
Chemical Abstracts, Abstract No. 105:61753 corresponding to US 4560716 (Dec. 24, 1985).

* cited by examiner

Primary Examiner—Porfirio Nazario-Gonzalez
(74) Attorney, Agent, or Firm—Quarles & Brady LLP

(57) ABSTRACT

An organic EL device is disclosed in which is placed a transparent water-capturing film comprising an easy-to-use organometallic compound illustrated by the chemical formula (1):

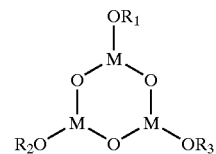

wherein, $R_1$, $R_2$ and $R_3$ are selected from the group consisting of alkyl group, aryl group, cycloalkyl group, heterocyclic group and acyl group having one carbon atom and above, and M is a trivalent metallic atom.

22 Claims, 3 Drawing Sheets

PDA t-BuPh-PTC

DRYING AGENT

The present invention relates to a dehumidifying agent or drying agent, and more particularly, to a drying agent comprising an organometallic compound.

DISCUSSION OF BACKGROUND

A drying agent conventionally used is an inorganic compound such as silica gel, Molecular Sieves (trade name for Linde Co.) calcium oxide, calcium chloride etc. Such a drying agent is used in the form of powder or particulate material.

Silica gel and Molecular Sieves are physical adsorption-type drying agents. Since water adsorbed thereby is driven off at high temperatures, they can not be used at high temperatures, but can be regenerated.

Calcium oxide and calcium chloride are chemisorption-type drying agents. Since water adsorbed thereby is not driven off at high temperatures, they can be used at high temperatures. However, they can not been regenerated.

When high dryness is required, more highly efficient chemisorption-type drying agents such as phosphorous pentoxide, barium oxide and so on are used. However, aforementioned drying agents are difficult to handle because of high reactivity, corrosivity, toxicity, etc. Since aforementioned inorganic drying agents are scattered and contaminate the environment because of being used in the form of powder or particulate, a prevention of dust is required.

Most of the conventional drying agents comprise a deliquescent inorganic salt, water-soluble polymer or hygroscopic resin or a mixture thereof, and are white. However, there are a few transparent drying agents. Therefore, when they are used for a drying agent for an organic electroluminescent (hereinafter referred to as "organic EL") device, they have the disadvantage that the device can not be observed through the drying agent.

Further, since the conventional drying agents are almost white and do not so definitely change color and state, they have disadvantages that the confirmation of moisture absorption effect can be hardly made or the measure of renewal of the drying agent can be hardly determined. In order to solve such disadvantages, a technology for a dehumidifying agent or drying agent has been proposed, which comprises a deliquescent inorganic salt powder, a gelling agent and a colored powder having an average particle size of 0.001~100 μm, and which changes color and/or tone (for example, Unexamined Patent Publication (Kokai) No. 2001-46832.)

SUMMARY OF THE INVENTION

Therefore, the object of the present invention is to overcome the problems described above and to provide a drying agent capable of being used at high temperatures or extremely low humidity in a sealed container and confirming changes in color and/or tone of the drying agent due to the absorption of moisture.

According to the present invention, there is provided a drying agent formed of an organometallic compound illustrated by the formula (1)

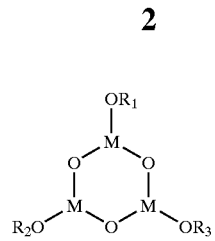

Formula 1 wherein, $R_1$, $R_2$ and $R_3$ are selected from the group consisting of alkyl group, aryl group, cycloalkyl group, heterocyclic group and acyl group having at least one carbon atom, and M is a trivalent metal atom.

In another aspect of the present invention, there is provided a drying agent formed of an organometallic compound illustrated by the formula (2)

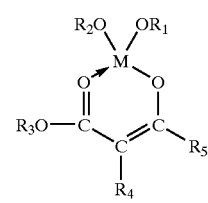

Formula 2 wherein, $R_1$, $R_2$, $R_3$, $R_4$ and $R_5$ are selected from the group consisting of alkyl group, aryl group, cycloalkyl group, heterocyclic group and acyl group having at least one carbon atom, and M is a trivalent metallic atom.

In still another aspect of the present invention, there is provided a drying agent formed of an organometallic compound illustrated by the formula (3)

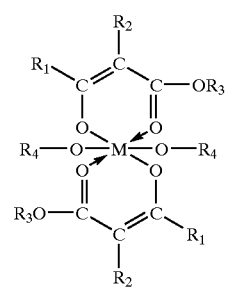

Formula 3 wherein, $R_1$, $R_2$, $R_3$ and $R_4$ are selected from the group consisting of alkyl group, aryl group, cycloalkyl group, heterocyclic group and acyl group having at least one carbon atom, and M is a quadrivalent metallic atom.

Optionally, the drying agent of the organometallic compounds is used in combination with an additional drying agent.

Optionally, the drying agent of the organometallic compounds is used in combination with an additional drying agent taking advantages of physical adsorption.

Optionally, the drying agent of the organometallic compounds is used in combination with an additional drying agent taking advantages of chemisorption.

Optionally, the drying agent of the organometallic compounds is used in combination with an additional drying agent taking advantage of the chemisorption and an additional drying agent taking advantage of the physical adsorption.

Optionally, the drying agent of the organometallic compounds is placed on an inner surface of the sealed container.

Optionally, the drying agent of the organometallic compounds is dispersed in a nonaqueous solvent and placed on an inside of the sealed container.

Optionally, the drying agent of the organometallic compounds includes a coloring agent.

According to the present invention, a film of drying agent can be formed by applying a solution of the drying agent formed of the organometallic compound to a place to be dried directly or by means of a supporting member, and drying the solution of the drying agent in a dried atmosphere. The film of drying agent thus formed is transparent and is capable of being seen through the drying agent. In one form of the present invention, a nonaqueous solution can be formed by mixing the organometallic compounds illustrated by the formulae (1), (2) and (3) as a drying agent with a nonaqueous solvent. The organometallic compounds illustrated by the formulae (1), (2) and (3) as a drying agent can be mixed with a coloring agent showing the rate of moisture absorption to form a drying agent containing the coloring agent which makes full use of the color development.

These and other objects and advantages of the present invention will be appreciated by those skilled in the art from the description given herein and the appended claims.

BRIEF DESCRIPTION OF THE DRAWINGS

The invention may be put into practice in various ways and a number of embodiments will be described by way of example to illustrate the invention with reference to the accompanying drawings, in which.

DETAILED DESCRIPTION OF THE PREFERRED EMBODIMENT

The present inventors have confirmed several effects of the drying agent of the present invention such as drying effect and so on in such a manner as described below:

Aluminum oxide octylate (available from HOPE PHARMACEUTICAL CO. under the trade name "OLIPE AOO") illustrated by the chemical formula (7), one of the organometallic compound (1), was dissolved in an organic solvent such as toluene, xylene and so on to form 48 wt%-containing solution. The 48 wt %-containing solution was applied on the surface of a glass substrate in a dried atmosphere such as dried air from which moisture was removed to the utmost and heated at a temperature of 120° C. for ten minutes to volatilize the organic solvent such as toluene, xylene, etc.

Figure 1:
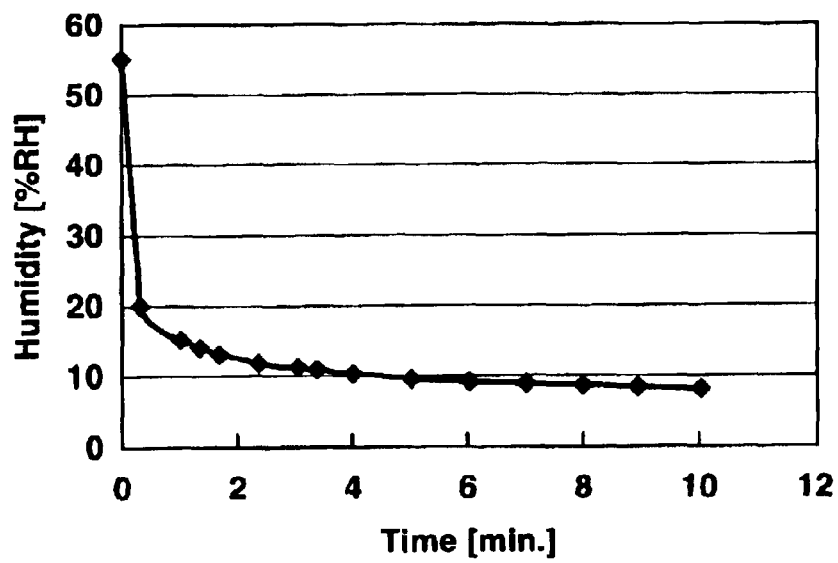
FIG. 1 is a graph showing the moisture-adsorption characteristics of the drying agent of the present invention.

Thereafter, the substrate was put in a desiccator filled with air from which moisture was removed to the utmost, and hermetically sealed. Then, the sensor section of a hygrometer (manufactured by CHINO under the trade name "MODEL HN-K") was inserted into the desiccator to measure humidity (FIG. 1.)

As a result, the initial humidity of 55% RH was sharply lowered by 40% to reach 15% RH after one minute, and was further lowered by 45% to reach 10% RH after ten minutes. It was proved that the drying agent of the present invention has an excellent drying effect.

Next, a comparative experiment was conducted on moisture-absorption effect between the drying agent of the present invention comprising the organometallic compound and a conventional drying agent CaO.

The surface of a 50×50 mm glass substrate was sand-blasted to form a concave portion having an area of 45×45 mm and thickness of 0.2 to 0.25 mm. After measuring the weight of the substrate, the substrate was put in an atmosphere of dried nitrogen. Then, the substrate was coated with 350 $\mu$l of solution containing 45 wt % of aluminum oxide octylate (available from HOPE PHARMACEUTICAL CO. under the trade name "OLIPE AOO") illustrated by the chemical formula (7), and dried at 120° C. for 20 minutes.

On the other hand, powdered CaO for comparison was dispersed uniformly on the concave portion of the glass substrate having the same size and shape as those of the glass substrate.

After drying, the substrate was taken out of atmosphere of dried nitrogen and weighed. Difference between this weight and the weight measured prior coating was taken as the weight of a sample.

Next, a sample was allowed to stand at an ordinary temperature and weighed after the elapse of a given time. The increments of weight were taken as water absorption.

Figure 2:
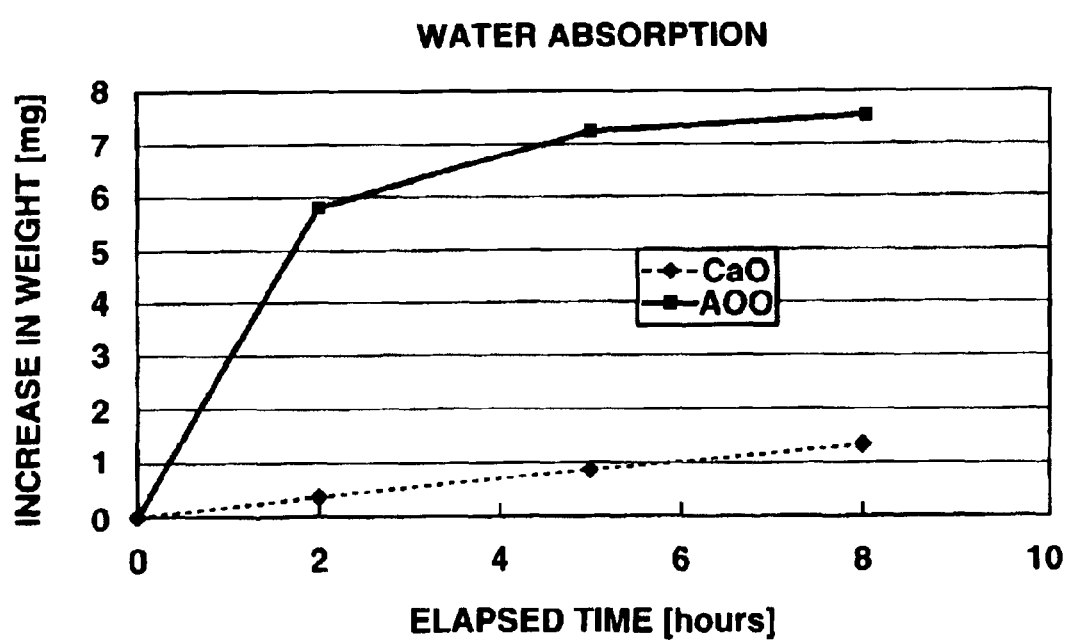
FIG. 2 is a graph showing the comparison of moisture-absorption characteristics between the drying agent of the present invention and CaO.

FIG. 2 is a graph showing the relationship between the elapsed time and the increments of the weight of the sample (water absorption.)

It is evident as shown in FIG. 2 that the drying agent of the present invention comprising an organometallic compound is superior to a conventional drying agent CaO in that the moisture absorption power of the former is approximately five times that of the latter per 1 mol of the drying agent.

For reasons stated above, it is shown that the organometallic compound of the present invention is an excellent drying agent.

Figure 3:
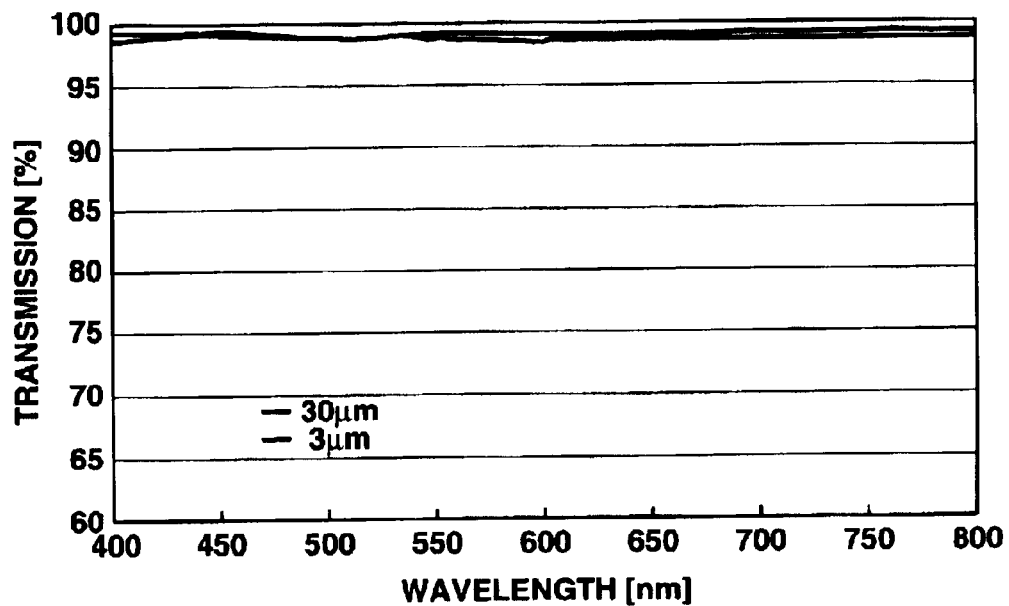
FIG. 3 is a graph showing the light transmittance of the drying agent of the present invention.

Next, the measured data on the transparency of the drying agent of the present invention comprising an organometallic compound is shown in FIG. 3.

A photometer manufactured by HITACHI under the trade name "U-2010-type spectrophotometer" was used to measure the light transmittance.

As shown in FIG. 3, the transparent drying agent of the present invention is in the form of a film having a thickness of 3 $\mu$m~30 $\mu$m comprising aluminum oxide octylate (available from HOPE PHARMACEUTICAL CO. under the trade name "OLIPE AOO") illustrated by the chemical formula (7), one of the organometallic compound (1), and transmits 95% and above of light having wavelength of 400 nm~800 nm. Accordingly, when the drying agent of the present invention is placed in a transparent container, it functions as a transparent drying agent. When the container is colored, the drying agent of the present invention functions as a drying agent which transmits the color of the container.

Further, when a closed container in which is placed the transparent drying agent of the present invention is formed as a transparent container, inside the container can be easily observed by taking advantage of characteristics of a closed container.

Next, a description is given on the mechanism of the function of the moisture absorption of the organometallic compound of the present invention:

It can be presumed that aluminum oxide octylate (available from HOPE PHARMACEUTICAL CO. under the trade name "OLIPE AOO") illustrated by the chemical formula (7), one of the organometallic compound (1) has moisture absorption/drying function, because it is reacted with water under heating according to the following reaction formula;

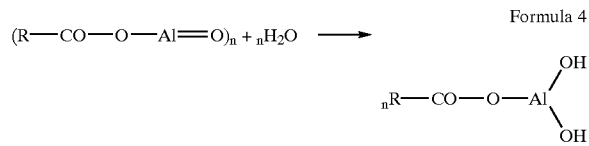

Formula 4

The reaction formula of the chelate-type metal complex containing Al with water shows a reaction partly similar to aluminum, alcoholate and aluminum chelate in respect to the reactivity shown in the above described chemical reaction formula (chemical formula 4.)

It can be presumed that the aluminum oxide octylate absorbs moisture in the reaction to function as a drying agent.

The present invention will be more clearly understood with reference to the following examples using the organometallic compound of the present invention.

EXAMPLES

Since the drying agent comprising the organometallic compound of the present invention is characterized in that it can be placed directly to a member constituting a closed container, examples are described below in which the drying agent of the present invention are mounted to an organic EL device, one of display devices, which has recently received considerable attention.

Since it has been known that a non-emitting portion which is known as a "dark spot" is generated and grown by a minute amount of water in the case of the above described organic EL device, the dehumidifying effect of the drying agent of the present invention is explained by making use of the generation-growth of the dark spot.

Example 1

Figure 4:
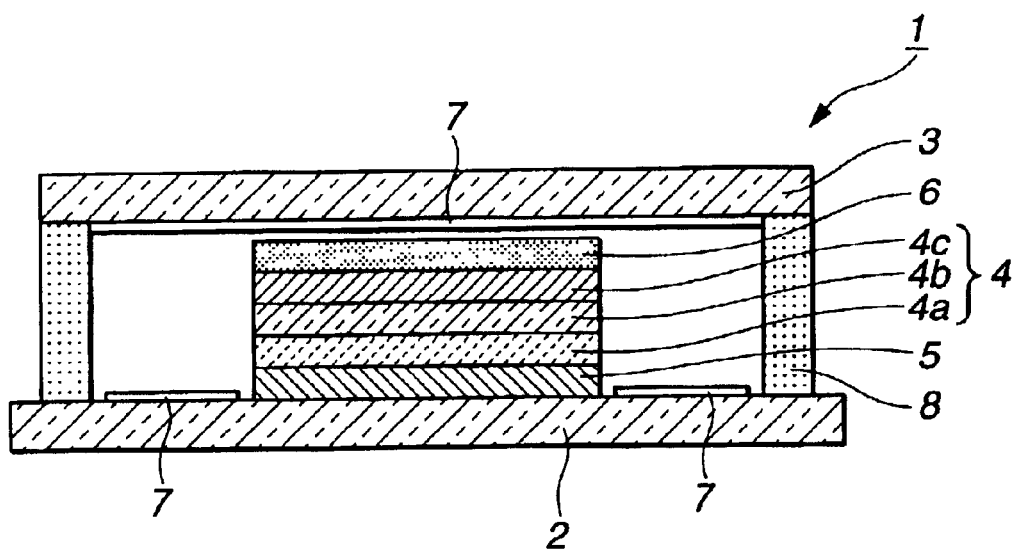
FIG. 4 is a side cross-sectional view showing the structure of an organic EL device.
Figure 5:
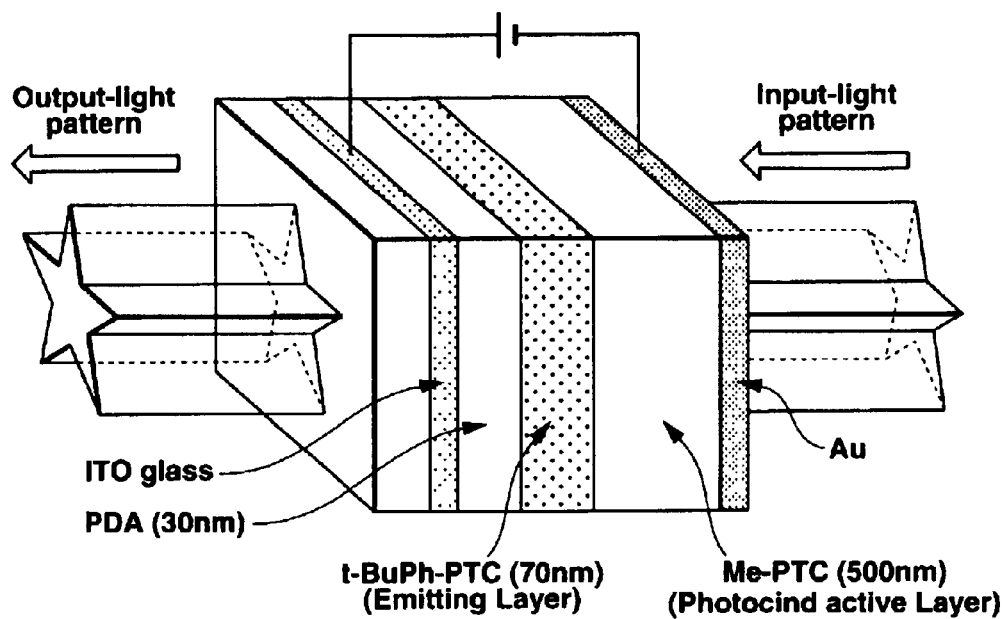
FIG. 5 is a block schematic diagram of an organic light-to-light conversion device.
Figure 5:
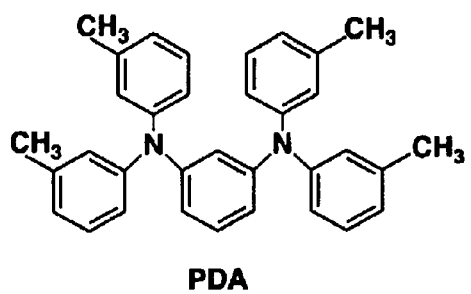
Figure 5:
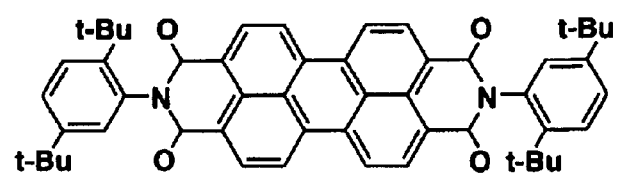

As shown in FIG. 4, the organic EL device comprises a device substrate 2 constituting a closed container of an insulating and transparent rectangle-shaped glass substrate. An anode 5 of ITO (indium tin oxide) film is formed on the device substrate 2 as a conductive material having transparency.

An organic EL film 4 of a thin film of an organic compound is stacked on the upper surface of the anode 5.

The organic EL film 4 comprises generally a hole injection film 4a, a hole transportation film 4b, and an electron transporting emitting film 4c.

A metal thin film as a cathode 6 is formed on the organic EL film 4.

A rectangle-shaped sealing container 3 as a sealing material for constituting a sealed container is fixed to the periphery of the base substrate 2 by, for example ultraviolet-curing resin type-adhesive 8 in an atmosphere of inert gas from which moisture is removed to the utmost, for example, in an atmosphere of dried nitrogen or dried air. Thereby, the organic EL device is protected.

The substrate and/or sealing container is hermetically sealed by the substrate 2, sealing container 3 and adhesive 8 is provided with the drying agent film 7.

The sealing container 3 was coated with only a solution containing 48 wt % of aluminum oxide octylate (available from HOPE PHARMACEUTICAL CO. under the trade name "OLIPE AOO") illustrated by the chemical formula (7), one of the organometallic compound (1), and dried in an atmosphere of dried air from which moisture was removed to the utmost. In such a manner as above described, a transparent film 30 μm thick of the organometallic compound was formed as drying means.

As shown in FIG. 4, while the organometallic compound as drying means may be applied to the whole inner surface of the plate member 3 constituting the sealing container, it may also be applied to the whole inner surface, except for an area of ultraviolet-curing epoxy resin (8) as a sealing part.

The organic EL device substrate was placed opposite to the sealing cup in an atmosphere of dried nitrogen from which moisture was removed to the utmost, and coated with ultraviolet-curing epoxy resin and dried to seal. Next, heating was carried out at a temperature of 85° C. for one hour to promote the curing reaction of the adhesive.

An accelerated life test was carried out on the emitting part of the organic EL device at a temperature of 85° C. and at relative humidity of 85%. Then, a microscopic examination was made on the emitting part of the organic EL device to confirm the growth of a non-emitting part (hereinafter referred to as a "dark spot") which is generated and grown in an organic EL device because of the presence of a minute amount of water. As a result, it was confirmed that while the initial diameter of the dark spot at the central portion of the organic EL device was 1 μm, it only grew up to 10 μm at the most after the elapse of 500 hours. Since a diameter of the dark spot of 10 μm and below can not be confirmed visually, there is no problem. Further, according to the present invention, the generation and growth of the dark spot at the periphery of the emitting part of the organic EL device were suppressed effectively. It is considered that 500 hours in the accelerated life test are equivalent to tens of thousands of times at an ordinary temperature and humidity.

For reasons stated above, it is evident that the drying agent of the present invention is an excellent drying agent.

It can be presumed that the chelate-type metal complex of trivalent metal containing aluminum which is one of the organometallic compounds of the present invention proceeds according to the reaction formula (4) and simultaneously functions as a drying agent by the following reaction.

The reaction of a chelate-type metal complex of the aforementioned organometallic compound containing aluminum with water proceeds by the following reaction formula (5):

Formula 5

$$Al(OR)_3 + 3H_2O = Al(OH)_3 + 3ROH$$

As shown in the reaction formula (5), three alkoxy groups are liberated from the aluminum complex and reacted with three hydroxyl groups of the water. It is therefore concluded that the aforementioned compound can be used as a drying agent, chemically removing the moisture.

The reaction of a chelate-type metal complex of metal other than the aforementioned aluminum metal complex with water proceeds by the following reaction formula (6):

Formula 6

$$M(OR1)(OR2)\ldots(ORn) + nH_2O = M(OH)_n + HOR1 + HOR2 + \ldots + HORn$$

As shown in the reaction formula (6), the organic compound corresponding to the valence of the metal is liberated and reacted with n hydroxyl groups. Therefore the compound illustrated by formulae (1), (2) and (3) can also be used as a drying agent chemically removing the moisture.

In a similar fashion to the above, the present inventors have discovered that the organometallic compounds illustrated by the formulae (1), (2) and (3) adsorb water molecules by hydrolysis. That is, the moisture in the periphery of the organic EL element reacts with the organometallic compound to separate M—O bond of 2n-member ring, and H and OH of the water molecule are reacted to form hydroxyl (OH) bond. The present inventors have discovered also that since one mole of the organometallic compound illustrated by the formulae (1), (2) and (3) reacts with three moles of water molecule to form hydroxide, the organometallic compound illustrated by the formulae (1), (2) and (3) has an adsorbing action on the moisture. The present inventors have conceived that the organometallic compound illustrated by the formulae (1), (2) and (3) has the action and principle upon which the organometallic compound illustrated by the formulae (1), (2) and (3) can be used as a drying agent for the organic EL element and have discovered that the organometallic compound illustrated by the formulae (1), (2) and (3) is effective for drying means. Examples of R of the formulae (1), (2) and (3) are described below but not limited thereto:

R is one selected from the group consisting of an alkyl group, alkenyl group, aryl group, cycloalkyl group, heterocyclic group and acyl group having at least one carbon atom. Alkyl group may be substituted or non-substituted and may be exemplified by a methyl group, ethyl group, propyl group, butyl group, sec-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, heneicosyl group, docosyl group, and the like and is preferably those having more than eight carbon atoms. Examples of substituted or non-substituted alkyl group are preferably those described below and an oligomer or polymer thereof may be used. Alkenyl group may be a vinyl group, allyl group, butenyl group, pentenyl group, hexynyl group and the like, and examples of substituted or non-substituted alkenyl group having eight or more carbon atoms may be preferably those described below. The oligomer or polymer thereof may be also used.

Aryl group may be substituted or non-substituted and may be exemplified by a phenyl group, tolyl group, 4-cyanophenyl group, biphenyl group, o,m,p-terphenyl group, naphthyl group, anthranyl group, phenanthrenyl group, fluorenyl group, 9-phenylanthranyl group, 9,10-diphenylanthranyl group, pyrenyl group, and the like and may be preferably those having eight or more carbon atoms. The oligomer or polymer thereof may be used.

Examples of substituted or non-substituted alkoxy group may be a methoxy group, n-butoxy group, tert-butoxy group, trichloromethoxy group, trifluoromethoxy group, and the like and may be preferably those having eight or more carbon atoms. The oligomer or polymer thereof may be used.

Examples of substituted or non-substituted cycloalkyl group may be a cyclopentyl group, cyclohexyl group, norbornane group, adamantane group, 4-methylcyclohexyl group, 4-cyanocyclohexyl group and the like and may be preferably those having eight or more carbon atoms. The oligomer or polymer thereof may be used.

Examples of substituted or non-substituted heterocyclic group may be a pyrrole group, pyrroline group, pyrazole group, pyrazoline group, imidazole group, triazole group, pyridine group, pyridazine group, pyrimidine group, pyrazine group, triazine group, indole group, benzimidazole group, purine group, quinoline group, isoquinoline group, cinorin group, quinoxaline group, benzquinoline group, fluorenone group, dicyanofluorenone group, carbazole group, oxazole group, oxadiazole group, thiazole group, thiadiazole group, benzoxazole group, benzothiazole group, benzotriazole group, bisbenzooxazole group, bisbenzothiazole group, bisbenzoimidazole group and the like. The oligomer or polymer thereof may be used.

Examples of substituted or non-substituted acyl group may be a formyl group, acetyl group, propionyl group, butyryl group, isobutyryl group, valeryl group, isovaleryl group, pivaloyl group, lauroyl group, myristoyl group, palmitoyl group, stearoyl group, oxalyl group, malonyl group, succinyl group, glutaryl group, adipoyl group, pimeloyl group, suberoyl group, azelaoyl group, sebacoyl group, acryloyl group, propioloyl group, methacryloyl group, crotonoyl group, isocrotonoyl group, oleoyl group, elaidoyl group, maleoyl group, fumaroyl group, citraconoyl group, mesaconoyl group, camphoroyl group, benzoyl group, phthaloyl group, isophthaloyl group, telephthaloyl group, naphthoyl group, toluoyl group, hydroatropoyl group, atropoyl group, cinnamoyl group, furoyl group, thenoyl group, nicotynoyl group, isonicotynoyl group, glycoloyl group, lactoyl group, glyceroyl group, tartronoyl group, maloyl group, tartharoyl group, tropoyl group, benziloyl group, salicyloyl group, anisoyl group, vaniloyl group, veratroyl group, piperonyloyl group, orotocatechoyl group, galloyl group, glyoxyloyl group, pyruvoyl group, acetoacetyl group, meso-oxalyl group, meso-oxalo group, oxalacetyl group, oxalaceto group, levulinoyl group, and the like. These acyl groups may be substituted with fluorine, chlorine, bromine, iodine and the like. The number of carbon atoms of the acyl group may be preferably eight and above. The oligomer or polymer thereof may be used.

Examples of the organometallic compound in which R is substituted with one of the above-described substituents and trivalent metal is aluminum are those illustrated by formulae (7), (8) and (9):

Formula 7

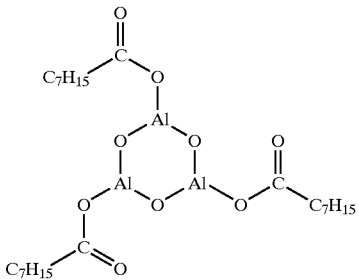

Formula 8

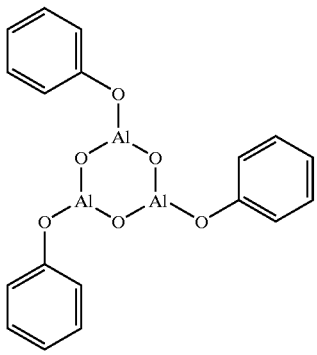

Formula 9

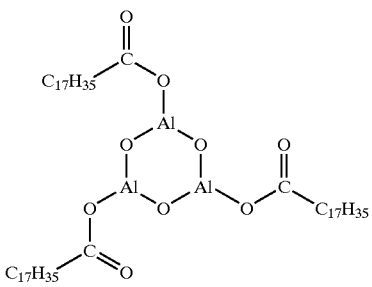

Further, the present inventors have discovered that the organometallic compounds illustrated by the formula (2) adsorb water molecules by hydrolysis. That is, the moisture in the periphery of the organic EL element reacts with the organometallic compound to separate M—O bond of 2n-member ring, and H and OH of the water molecule are reacted to form hydroxyl (OH) bond. The present inventors have discovered also that since one mole of the organometallic compound illustrated by the formula (2) reacts with three moles of water molecules to form hydroxide, the organometallic compound illustrated by the formula (2) has an adsorbing action on the moisture. The present inventors have conceived that the organometallic compound illustrated by the formula (2) has the action and principle upon which the organometallic compound illustrated by the formula (2) can be used as a drying agent for the organic EL element and have discovered that the organometallic compound illustrated by the formula (2) is effective for drying means. Examples of $R_1$, $R_2$, $R_3$, $R_4$ and $R_5$ of the formula (2) are described below but not limited thereto:

Each of $R_1$, $R_2$, $R_3$, $R_4$ and $R_5$ of the formula (2) are one selected from the group consisting of alkyl group, alkenyl group, aryl group, cycloalkyl group, heterocyclic group and acyl group. Alkyl group may be substituted or non-substituted and may be exemplified by a methyl group, ethyl group, propyl group, butyl group, sec-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, heneicosyl group, docosyl group, and the like and is preferably those having eight or more carbon atoms. Examples of substituted or non-substituted alkyl group are preferably those described below and an oligomer or polymer thereof may be used. Alkenyl group may be a vinyl group, allyl group, butenyl group, pentenyl group, hexynyl group, and the like, and examples of substituted or non-substituted alkenyl group having eight or more carbon may be preferably those described below. The oligomer or polymer thereof may be also used.

Aryl group may be substituted or non-substituted and may be exemplified by a phenyl group, tolyl group, 4-cyanophenyl group, biphenyl group, o,m,p-terphenyl group, naphthyl group, anthranyl group, phenanthrenyl group, fluorenyl group, 9-phenylanthranyl group, 9,10-diphenylanthranyl group, pyrenyl group and the like. The oligomer or polymer thereof may be used.

Examples of substituted or non-substituted alkoxy group may be a methoxy group, n-butoxy group, tert-butoxy group, trichloromethoxy group, trifluoromethoxy group and the like. The oligomer or polymer thereof may be used.

Examples of substituted or non-substituted cycloalkyl group may be a cyclopentyl group, cyclohexyl group, norbornane group, adamantane group, 4-methylcyclohexyl group, 4-cyanocyclohexyl group and the like. The oligomer or polymer thereof may be used.

Examples of substituted or non-substituted heterocyclic group may be a pyrrole group, pyrroline group, pyrazole group, pyrazoline group, imidazole group, triazole group, pyridine group, pyridazine group, pyrimidine group, pyrazine group, triazine group, indole group, benzimidazole group, purine group, quinoline group, isoquinoline group, cinorin group, quinoxaline group, benzquinoline group, fluorenone group, dicyanofluorenone group, carbazole group, oxazole group, oxadiazole group, thiazole group, thiadiazole group, benzoxazole group, benzothiazole group, benzotriazole group, bisbenzooxazole group, bisbenzothiazole group, bisbenzoimidazole group and the like. The oligomer or polymer thereof may be used.

Examples of substituted or non-substituted acyl group may be a formyl group, acetyl group, propionyl group, butyryl group, isobutyryl group, valeryl group, isovaleryl group, pivaloyl group, lauroyl group, myristoyl group, palmitoyl group, stearoyl group, oxalyl group, malonyl group, succinyl group, glutaryl group, adipoyl group, pimeloyl group, suberoyl group, azelaoyl group, sebacoyl group, acryloyl group, propioloyl group, methacryloyl group, crotonoyl group, isocrotonoyl group, oleoyl group, elaidoyl group, maleoyl group, fumaroyl group, citraconoyl group, mesaconoyl group, camphoroyl group, benzoyl group, phthaloyl group, isophthaloyl group, telephthaloyl group, naphthoyl group, toluoyl group, hydroatropoyl group, atropoyl group, cinnamoyl group, furoyl group, thenoyl group, nicotynoyl group, isonicotynoyl group, glycoloyl group, lactoyl group, glyceroyl group, tartronoyl group, maloyl group, tartharoyl group, tropoyl group, benziloyl group, salicyloyl group, anisoyl group, vaniloyl group, veratroyl group, piperonyloyl group, orotocatechoyl group, galloyl group, glyoxyloyl group, pyruvoyl group, acetoacetyl group, meso-oxalyl group, meso-oxalo group, oxalacetyl group, oxalaceto group, levulinoyl group and the like. These acyl groups may be substituted with fluorine, chlorine, bromine, iodine and the like. The oligomer or polymer thereof may be used.

Examples of the organometallic compound in which each of $R_1$, $R_2$, $R_3$, $R_4$ and $R_5$ is substituted with one of the above-described substituents and trivalent metal is aluminum are organometallic complex compound illustrated by formulae (10), (11), (12) and (13):

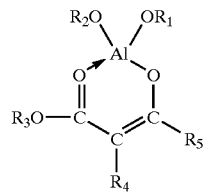

Formula 10

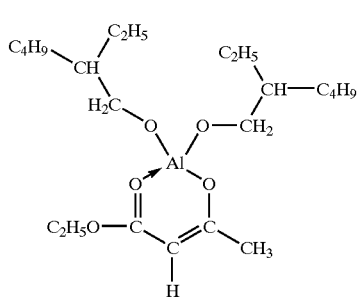

Formula 11

Aluminium-di-2-ethylhexyloxide-mono-Ehtyl aceto acetate Chelope-EH-2

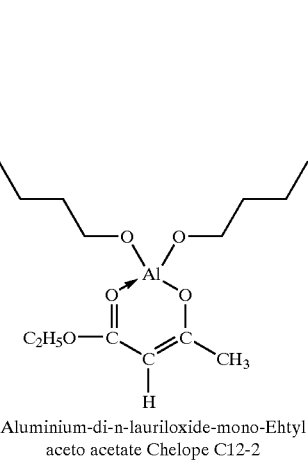

Formula 12

Aluminium-di-n-lauriloxide-mono-Ehtyl aceto acetate Chelope C12-2

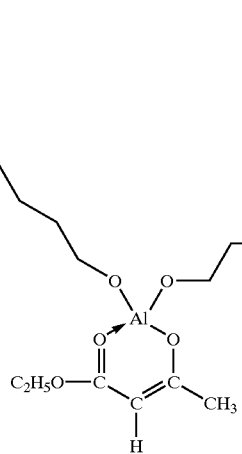

Formula 13

Aluminium-di-2-methylnonyloxide-mono-Ehtyl aceto acetate Chelope C10-2

An example of the organometallic compound in which the trivalent metal is lanthanum is the organometallic complex compound illustrated by the formula (14):

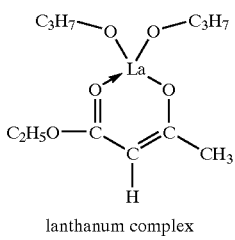

lanthanum complex

An example of the organometallic compound in which the trivalent metal is yttrium is the organometallic complex compound illustrated by the formula (15):

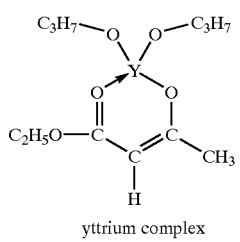

yttrium complex

An example of the organometallic compound in which the trivalent metal is gallium is the organometallic complex compound illustrated by the formula (16):

Formula 16

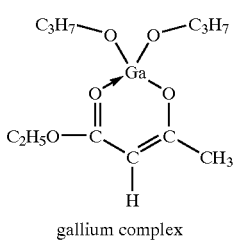

gallium complex

In each of Examples 2, 3 and 4 described below, the compounds illustrated by the chemical formulae (11), (12) and (13) which are examples of the above described compounds were used respectively as a drying agent for an organic EL device.

Example 2

Chemical Formula (11)

An inner surface of a sealing glass was coated with a toluene-50% solution of a compound illustrated by the chemical formula (11) (HOPE PHARMACEUTICAL CO. under the trade name "Chelope-EH-2") and dried to form a substrate. By using the substrate a sealing container was made by using adhesive. The same procedures as those of Example 1 were repeated except for the above described procedures.

Next, the sealing container was heated at a temperature of 85° C. for one hour to promote the curing reaction of the adhesive to form an organic EL device.

The state of emission of the organic EL device was observed by a microscope.

Then, after an accelerated life test was carried out on the emitting part of the organic EL device at a temperature of 85° C. and at relative humidity of 85%, the growth of the dark spot was observed. After the elapse of 100 hours, the device was taken out of an accelerated life test chamber, and the state of emission was observed by means of a microscope. As a result, it was confirmed that the dark spot was hardly grown. Further, the generation and growth of the dark spot at the periphery of the organic EL device was hardly different from that at the central portion of the organic EL device.

For reasons stated above, it is evident that the drying agent of the present invention is an excellent drying agent.

Example 3

Chemical Formula (12)

An organic EL device was prepared by using the same procedures as those of Example 1, except that the compound of "Chelope-C10-2," trade name for HOPE PHARMACEUTICAL CO. was used as the compound illustrated by the chemical formula (12).

The state of emission of the organic EL device was observed by a microscope. Then, after an accelerated life test was carried out on the emitting part of the organic EL device at a temperature of 85° C. and at relative humidity of 85%, the growth of the dark spot was observed. After the elapse of 100 hours, the device was taken out of an accelerated life test chamber, and the state of emission was observed by means of a microscope. As a result, it was confirmed that the dark spot was hardly grown. Further, the generation and growth of the dark spot at the periphery of the organic EL device was hardly different from that at the central portion of the organic EL device.

For reasons stated above, it is evident that the drying agent of the present invention is an excellent drying agent.

Example 4

Chemical Formula (13)

An organic EL device was prepared by using the same procedures as those of Example 1, except that the compound of "Chelope-C12-2" trade name for HOPE PHARMACEUTICAL CO. was used as the compound illustrated by the chemical formula (13).

The state of emission of the organic EL device was observed by a microscope. Then, after an accelerated life test was carried out on the emitting part of the organic EL device at a temperature of 85° C. and at relative humidity of 85%, the growth of the dark spot was observed. After the elapse of 100 hours, the device was taken out of an accelerated life test chamber, and the state of emission was observed by means of a microscope. As a result, it was confirmed that the dark spot was hardly grown. Further, the generation and growth of the dark spot at the periphery of the organic EL device was hardly different from that at the central portion of the organic EL device.

For reasons stated above, it is evident that the drying agent of the present invention is an excellent drying agent.

Next, Examples 5, 6, 7, 8, and 9 were carried out in which a central metal atom of "Chelope"-series (trade name for an organometallic complex as drying means manufactured by HOPE PHARMACEUTICAL CO.) were replaced.

Example 5

Chemical Formula (14)

An inner surface of a sealing glass was coated with a solution of La complex shown by chemical formula (14) as a drying agent and dried to form a substrate. By using the substrate a sealing container was made by using adhesive. An organic EL device was prepared by using the same procedures as those of Example 1, except for the above described procedures.

The state of emission of the organic EL device was confirmed by a microscope. Then, after an accelerated life test was carried out on the emitting part of the organic EL device at a temperature of 85° C. and at relative humidity of 85%, the growth of the dark spot was confirmed. After the elapse of 100 hours, the device was taken out of an accelerated life test chamber, and the state of emission was observed by means of a microscope. As a result, it was confirmed that the dark spot was hardly grown. Further, the generation and growth of the dark spot at the periphery of the organic EL device was hardly different from that at the central portion of the organic EL device.

The area of non-emitting part of the organic EL device of Example 5 was smaller than that without water-capturing agent.

For reasons stated above, it is evident that the drying agent of the present invention is an excellent drying agent.

Example 6

Chemical Formula 15

A novel organometallic complex (chemical formula 15) was synthesized by replacing a central metal atom of "Chelope"-series (trade name for an organometallic complex as drying means manufactured by HOPE PHARMACEUTICAL CO.) with Y. The same procedures as those of Example 1 were repeated except such that.

Next, vacuum operation was stopped. Sealing was carried out in an atmosphere of dried nitrogen. An inner surface of a sealing glass was coated with a solution of Y complex and dried to form a substrate. An organic EL device was prepared by bonding the substrate with adhesive.

Next, the organic EL device was heated at a temperature of 85° C. for one hour to promote the curing reaction of the adhesive. The state of emission of the organic EL device was observed by a microscope.

Then, after an accelerated life test was carried out on the emitting part of the organic EL device at a temperature of 85° C. and at relative humidity of 85%, the growth of the dark spot was observed. After the elapse of 100 hours, the device was taken out of an accelerated life test chamber, and the state of emission was observed by means of a microscope. As a result, it was confirmed that the dark spot was hardly grown. While Y complex was inferior to La complex in the effect of drying agent, the area of non-emitting part of the organic EL device of Example 6 was smaller than that without a drying agent. Further, the generation and growth of the dark spot at the periphery of the organic EL device of Example 6 was hardly different from that at the central portion of the organic EL device.

For reasons stated above, it is evident that the drying agent of the present invention is an excellent drying agent.

Example 7

Chemical Formula 16

A novel organometallic complex (chemical formula 16) was synthesized by replacing a central metal atom of "Chelope"-series (trade name for an organometallic complex as drying means manufactured by HOPE PHARMACEUTICAL CO.) with Ga. The same procedures as those of Example 1 were repeated except such that.

An inner surface of a sealing glass was coated with a solution of Ga complex and dried to form a substrate. An organic EL device was prepared by bonding the substrate with adhesive.

Next, the organic EL device was heated at a temperature of 85° C. for one hour to promote the curing reaction of the adhesive. The state of emission of the organic EL device was observed by a microscope.

Then, after an accelerated life test was carried out on the emitting part of the organic EL device at a temperature of 85° C. and at relative humidity of 85%, the growth of dark spot was observed. After the elapse of 100 hours, the device was taken out of an accelerated life test chamber, and the state of emission was observed by means of a microscope. As a result, it was confirmed that the dark spot was hardly grown. While Ga complex was inferior to La complex in the effect of drying agent, the area of non-emitting part of the organic EL device of Example 7 was smaller than that without a water-capturing agent.

For reasons stated above, it is evident that the drying agent of the present invention is an excellent drying agent.

Further, the present inventors have discovered that the organometallic compounds illustrated by the formula (3) adsorb water molecules by hydrolysis. That is, the moisture in the periphery of the organic EL element reacts with the organometallic compound to separate M—O bond of 2n-member ring, and H and OH of the water molecule are reacted to form hydroxyl (OH) bond. The present inventors have discovered also that since one mole of the organometallic compound illustrated by the formula (3) reacts with three moles of water molecule to form hydroxide, the organometallic compound illustrated by the formula (3) has an adsorbing action on the moisture. The present inventors have conceived that the organometallic compound illustrated by the formula (3) has the action and principle upon which the organometallic compound illustrated by the formula (3) can be used as a drying agent for the organic EL element and have discovered that the organometallic compound illustrated by the formula (3) is effective for drying means. Examples of $R_1$, $R_2$, $R_3$, and $R_4$ of the formula (3) are described below but not limited thereto:

Each of $R_1$, $R_2$, $R_3$ and $R_4$ of the formula (3) are selected from the group consisting of alkyl group, alkenyl group, aryl group, cycloalkyl group, heterocyclic group and acyl group having more than one carbon atom. Alkyl group may be substituted or non-substituted and may be exemplified by a methyl group, ethyl group, propyl group, butyl group, sec-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, heneicosyl group, docosyl group, and the like and is preferably those having eight or more carbon atoms. Examples of substituted or non-substituted alkyl group are preferably those described below and an oligomer or polymer thereof may be used. Alkenyl group may be a vinyl group, allyl group, butenyl group, pentenyl group, hexynyl group, and the like, and examples of substituted or non-substituted alkenyl group having eight or more carbon atoms may be preferably those described below. The oligomer or polymer thereof may be also used.

Aryl group may be substituted or non-substituted and may be exemplified by a phenyl group, tolyl group, 4-cyanophenyl group, biphenyl group, o,m,p-terphenyl group, naphthyl group, anthranyl group, phenanthrenyl group, fluorenyl group, 9-phenylanthranyl group, 9,10-diphenylanthranyl group, pyrenyl group and the like. The oligomer or polymer thereof may be used.

Examples of substituted or non-substituted alkoxy group may be a methoxy group, n-butoxy group, tert-butoxy group, trichloromethoxy group, trifluoromethoxy group and the like. The oligomer or polymer thereof may be used.

Examples of substituted or non-substituted cycloalkyl group may be a cyclopentyl group, cyclohexyl group, norbornane group, adamantane group, 4-methylcyclohexyl group, 4-cyanocyclohexyl group and the like. The oligomer or polymer thereof may be used.

Examples of substituted or non-substituted heterocyclic group may be a pyrrole group, pyrroline group, pyrazole group, pyrazoline group, imidazole group, triazole group, pyridine group, pyridazine group, pyrimidine group, pyrazine group, triazine group, indole group, benzimidazole group, purine group, quinoline group, isoquinoline group, cinorin group, quinoxaline group, benzquinoline group, fluorenone group, dicyanofluorenone group, carbazole group, oxazole group, oxadiazole group, thiazole group, thiadiazole group, benzoxazole group, benzothiazole group, benzotriazole group, bisbenzooxazole group, bisbenzothiazole group, bisbenzoimidazole group. The oligomer or polymer thereof may be used.

Examples of substituted or non-substituted acyl group may be a formyl group, acetyl group, propionyl group, butyryl group, isobutyryl group, valeryl group, isovaleryl group, pivaloyl group, lauroyl group, myristoyl group, palmitoyl group, stearoyl group, oxalyl group, malonyl group, succinyl group, glutaryl group, adipoyl group, pimeloyl group, suberoyl group, azelaoyl group, sebacoyl group, acryloyl group, propioloyl group, methacryloyl group, crotonoyl group, isocrotonoyl group, oleoyl group, elaidoyl group, maleoyl group, fumaroyl group, citraconoyl group, mesaconoyl group, camphoroyl group, benzoyl group, phthaloyl group, isophthaloyl group, telephthaloyl group, naphthoyl group, toluoyl group, hydroatropoyl group, atropoyl group, cinnamoyl group, furoyl group, thenoyl group, nicotynoyl group, isonicotynoyl group, glycoloyl group, lactoyl group, glyceroyl group, tartronoyl group, maloyl group, tartharoyl group, tropoyl group, benziloyl group, salicyloyl group, anisoyl group, vaniloyl group, veratroyl group, piperonyloyl group, orotocatechoyl group, galloyl group, glyoxyloyl group, pyruvoyl group, acetoacetyl group, meso-oxalyl group, meso-oxalo group, oxalacetyl group, oxalaceto group, levulinoyl group, and the like. These acyl groups may be substituted with fluorine, chlorine, bromine, iodine and the like. The oligomer or polymer thereof may be used.

An example of the organometallic compound in which each of $R_1$, $R_2$, $R_3$ and $R_4$ is substituted with one of the above-described substituents and tetravalent metal is germanium is the organometallic complex compound illustrated by formula (17):

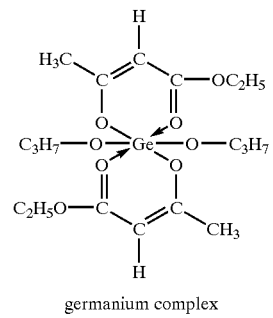

germanium complex

Formula 17

An example of the organometallic compound in which R is substituted with the above-described substituents and tetravalent metal is silicon is the organometallic complex compound illustrated by formula (18):

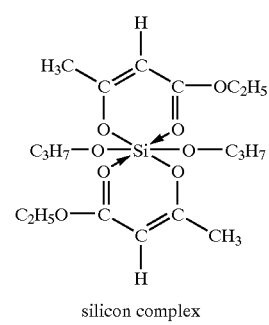

silicon complex

Formula 18

Example 8

Chemical Formula 17

A novel organometallic complex (chemical formula 17) was synthesized by replacing a central metal atom of "Chelope"-series (trade name for an organometallic complex as drying means manufactured by HOPE PHARMACEUTICAL CO.) with Ge. The same procedures as those of Example 1 were repeated except such that.

An inner surface of a sealing glass was coated with a solution of Ge complex and dried to form a substrate. An organic EL device was prepared by bonding the substrate with adhesive. Next, the organic EL device was heated at a temperature of 85° C. for one hour to promote the curing reaction of the adhesive.

The state of emission of the organic EL device was observed by a microscope.

Then, after an accelerated life test was carried out on the emitting part of the organic EL device at a temperature of 85° C. and at relative humidity of 85%, the growth of dark spot was observed. After the elapse of 100 hours, the device was taken out of an accelerated life test chamber, and the state of emission was observed by means of a microscope. As a result, it was confirmed that the dark spot was hardly grown. Further, the generation and growth of the dark spot at the periphery of the organic EL device of Example 8 was hardly different from that at the central portion of the organic EL device.

For reasons stated above, it is evident that the drying agent of the present invention is an excellent drying agent.

Example 9

Chemical Formula 18

A novel organometallic complex (chemical formula 18) was synthesized by replacing a central metal atom of "Chelope"-series (trade name for an organometallic complex as drying means manufactured by HOPE PHARMACEUTICAL CO.) with Si. The organometallic complex thus obtained was dissolved in toluene. The same procedures as those of Example 1 were repeated except such that.

An inner surface of a sealing glass was coated with a solution of Si complex and dried to form a substrate. Next, an organic EL device was prepared by bonding the substrate with adhesive. The organic EL device was heated at a temperature of 85° C. for one hour to promote the curing reaction of the adhesive. The state of emission of the organic EL device was observed by a microscope. Then, after an accelerated life test was carried out on the emitting part of the organic EL device at a temperature of 85° C. and at relative humidity of 85%, the growth of the dark spot was observed. After the elapse of 100 hours, the device was taken out of an accelerated life test chamber, and the state of emission was observed by means of a microscope. As a result, it was confirmed that the dark spot was hardly grown.

For reasons stated above, it is evident that the drying agent of the present invention is an excellent drying agent.

Since the compounds illustrated by the chemical formulae (1), (2) and (3) can be dissolved in a nonaqueous aromatic organic solvent such as toluene, xylene, etc. or a nonaqueous aliphatic organic solvent, it can be presumed that they have functions and principles that they can be used in combination with a generally-used drying agent dispersed in such an organic solvent.

A drying agent film 7 is formed as a drying agent on the inner surface of the sealing container 2. The several structures as described below can be considered suitable for the drying agent film 7. First, the drying agent film 7 comprises only the compounds illustrated by the chemical formulae (1), (2) and (3) as well as another organometallic compound. Since the drying agent film 7 comprising the compounds illustrated by the chemical formulae (1), (2) and (3) as well as another organometallic compound can be obtained as a solution of an organometallic compound containing n-valent metal in an aromatic organic solvent such as toluene, xylene, etc. or aliphatic organic solvent, such a solution can be applied to the inner surface of the substrate 3, for example by printing method, spincoat method, coating method, etc. and dried to form a film.

Further, the drying agent film 7 can be formed by adding any other drying agent into the drying agent film 7 comprising the compounds illustrated by the chemical formulae (1), (2) and (3) and another organometallic compound. Suitable as the drying agent added into the drying agent film are a substance chemically adsorbing water molecule (chemisorption-type drying agent), a substance physically adsorbing water molecule (physical adsorption-type drying agent), and any other substances.

A chemisorption-type drying agent may be a metallic oxide, sulfate, metallic halide, perchlorate, metal, etc. The drying effect of such a substance can be increased by dispersing such a substance in a solution prepared by dissolving the compounds illustrated by the chemical formulae (1), (2) and (3) and another organometallic compound in an aromatic organic solvent such as toluene, xylene, etc. or aliphatic organic solvent.

Examples of an alkaline metal oxide as a metallic oxide are sodium oxide ($Na_2O$), potassium oxide ($K_2O$), etc. Examples of an alkaline earth metal oxide as a metallic oxide are calcium oxide (CaO), barium oxide (BaO), magnesium oxide (MaO), etc. Examples of the sulfate are lithium sulfate ($Li_2SO_4$), sodium sulfate ($Na_2SO_4$), calcium sulfate ($CaSO_4$), magnesium sulfate ($MgSO_4$), cobalt sulfate ($CoSO_4$), gallium sulfate ($Ga_2(SO_4)$) 3), titanium sulfate ($Ti(SO_4)_2$), nickel sulfate ($NiSO_4$), etc. These salts are preferably used in a form of anhydrous salt.

Examples of the metallic halide are calcium chloride ($CaCl_2$), magnesium chloride ($MaCl_2$), strontium chloride ($SrCl_2$), yttrium chloride ($YCl_2$), copper chloride ($CuCl_2$), cesium fluoride (CsF), tantalum fluoride (TaF), niobium fluoride (NbF), calcium bromide ($CaBr_2$), cerium bromide ($CeBr_2$), selenium bromide ($SeBr_2$), vanadium bromide ($VBr_2$), magnesium bromide ($MgBr_2$), barium iodide ($BaI_2$), magnesium iodide ($MgI_2$), etc. These metallic halides may be preferably used in a form of anhydrous salt.

Examples of the perchlorate are barium perchlorate ($Ba(ClO_4)_2$), magnesium perchlorate ($Mg(ClO_4)_2$), etc. These perchlorates may be preferably used in a form of anhydrous salt.

Examples of the substance physically adsorbing water molecule, that is, physical adsorption-type drying agent are zeolite, silica gel, activated alumina, titanium oxide, carbon, carbon-nano-tube, fullerene, etc. The drying effect of such a substance can be increased by dispersing such a substance in a solution prepared by dissolving the compounds illustrated by the chemical formulae (1), (2) and (3) and another organometallic compound in an aromatic organic solvent such as toluene, xylene, etc. or aliphatic organic solvent.

Films of an anode, an organic EL film and a cathode are formed on the substrate 2 by PVD (physical vapor deposition), and then a CuPC as a buffer film and a GeO as a protective film are physically deposited. The drying agent film 7 comprising the compounds illustrated by the chemical formulae (1), (2) and (3) and any other organometallic compounds can be placed on the substrate 2 to form a non-permeable film.

The drying effect can be further increased by dispersing a drying agent such as the above described chemisorption-type drying agent or physical adsorption-type drying agent on the drying agent film of the present invention.

Example 10

In Example 10, a chemisorption-type drying agent was mixed with the drying agent of Example 1 and dispersed therein.

The same procedures as those of Example 1 were repeated except that: Calcium oxide (CaO), a chemisorption-type drying agent, was mixed with the solution containing 48 wt % of aluminum oxide octylate (available from HOPE PHARMACEUTICAL CO., under the trade name "OLIPE AOO") illustrated by the chemical formula (7) which is an organometallic compound illustrated by the chemical formula (2) in the weight ratio of 1:1 and dispersed therein to prepare dispersion which was then applied to a sealing container in a dried atmosphere. Then, an organic EL device was prepared in the same manner as that of Example 1.

A microscopic examination was made on the emitting part of the organic EL device to confirm the growth of dark spot at a temperature of 85° C. and at relative humidity of 85%. As a result, it was confirmed that while the initial diameter of the dark spot of the central portion of the organic EL device was 1 $\mu$m, it grew only up to 7 $\mu$m at the most after the elapse of 500 hours. Further, the generation and growth of the dark spot at the periphery of the emitting part of the organic EL device were not different from those of the central portion.

For reasons stated above, it is evident that the drying agent of the present invention is an excellent drying agent.

Example 11

In Example 11, a physical adsorption-type drying agent was mixed with the drying agent of Example 1 and dispersed therein.

The same procedures as those of Example 1 were repeated except that: Zeolite, a physical adsorption-type drying agent, was mixed with the solution containing 48 wt % of aluminum oxide octylate (available from HOPE PHARMACEUTICAL CO., under the trade name "OLIPE AOO") illustrated by the chemical formula (7) which is an organometallic compound illustrated by the chemical formula (1) in the weight ratio of 1:1 and dispersed therein to prepare dispersion which was then applied to a sealing container in a dried atmosphere. Then, an organic EL device was prepared in the same manner as that of Example 1.

An accelerated life test was carried out on the emitting part of the organic EL device at a temperature of 85° C. and at relative humidity of 85%. Then, a microscopic examination was made on the emitting part of the organic EL device to confirm the growth of the dark spot. As a result, it was confirmed that while the initial diameter of the dark spot at the central portion of the organic EL device was 1 m, it grew only up to 9 $\mu$m at the most after the elapse of 500 hours. Further, the generation and growth of the dark spot at the periphery of the emitting part of the organic EL device were not different from those of the central portion.

For reasons stated above, it is evident that the drying agent of the present invention is an excellent drying agent.

Example 12

In Example 12, a chemisorption-type drying agent and a physical adsorption-type drying agent were mixed with the drying agent of Example 3 and dispersed therein.

The same procedures as those of Example 1 were repeated except that: Calcium oxide (CaO) (hereinafter referred to as "X"), a chemisorption-type drying agent, and zeolite (hereinafter referred to as "Y"), a physical adsorption-type drying agent, were mixed with the solution containing 48 wt % of aluminum oxide octylate (hereinafter referred to as "Z") (available from HOPE PHARMACEUTICAL CO. under the trade name "OLIPE AOO") illustrated by the chemical formula (7) which is an organometallic compound illustrated by the chemical formula (1) in the weight ratio of 2Z:1x:1Y and dispersed therein to prepare dispersion which was then applied to a sealing container in a dried atmosphere. Then, an organic EL device was prepared in the same manner as that of Example 1.

A microscopic examination was made on the emitting part of the organic EL device to confirm the growth of dark spot at a temperature of 85° C. and at relative humidity of 85%. As a result, it was confirmed that while the initial diameter of the dark spot of the central portion of the organic EL device was 1 $\mu$m, it grew only up to 7 $\mu$m at the most after the elapse of 500 hours. Further, the generation and growth of the dark spot at the periphery of the emitting part of the organic EL device were not different from those of the central portion.

For reasons stated above, it is evident that the drying agent of the present invention is an excellent drying agent.

Example 13

In Example 13, a chemisorption-type drying agent was mixed with the drying agent of Example 4 and dispersed therein.

The same procedures as those of Example 4 were repeated except that:, Calcium oxide (CaO), a chemisorption-type drying agent, was mixed with the solution containing 48 wt % of aluminum oxide octylate (available from HOPE PHARMACEUTICAL CO. under the trade name "OLIPE AOO") illustrated by the chemical formula (7) which is an organometallic compound illustrated by the chemical formula (1) in the weight ratio of 1:1 and dispersed therein to prepare dispersion which was then applied to a sealing container in a dried atmosphere. Then, an organic EL device was prepared in the same manner as that of Example 4.

An accelerated life test was carried out on the emitting part of the organic EL device at a temperature of 85° C. and at relative humidity of 85%. Then, a microscopic examination was made on the emitting part of the organic EL device to confirm the growth of the dark spot. As a result, it was confirmed that while the initial diameter of the dark spot was 1 t™ m, it grew only up to 7 $\mu$m at the most after the elapse of 500 hours. Further, the generation and growth of the dark spot at the periphery of the emitting part of the organic EL device were not different from those of the central portion.

For reasons stated above, it is evident that the drying agent of the present invention is an excellent drying agent.

Example 14

In Example 14, a physical adsorption-type drying agent was mixed with the drying agent of Example 5 and dispersed therein.

The same procedures as those of Example 5 were repeated except that: Zeolite, a physical adsorption-type drying agent, was mixed with the solution containing 48 wt % of aluminum oxide octylate (available from HOPE PHARMACEUTICAL CO., under the trade name "OLIPE AOO") illustrated by the chemical formula (7) which is an organometallic compound illustrated by the chemical formula (1) in the weight ratio of 1:1 and dispersed therein to prepare dispersion which was then applied to a sealing container in a dried atmosphere. Then, an organic EL device was prepared in the same manner as that of Example 5.

An accelerated life test was carried out on the emitting part of the organic EL device at a temperature of 85° C. and at relative humidity of 85%. Then, a microscopic examination was made on the emitting part of the organic EL device to confirm the growth of the dark spot. As a result, it was confirmed that while the initial diameter of the dark spot was 1 $\mu$m, it grew only up to 9 $\mu$m at the most after the elapse of 500 hours. Further, the generation and growth of the dark spot at the periphery of the emitting part of the organic EL device were not different from those of the central portion.

For reasons stated above, it is evident that the drying agent of the present invention is an excellent drying agent.

Example 15

In Example 15, a chemisorption-type drying agent and a physical adsorption-type drying agent were mixed with the drying agent of Example 6 and dispersed therein.

The same procedures as those of Example 6 were repeated except that: Calcium oxide (CaO) (hereinafter referred to as "X"), a chemisorption-type drying agent, and zeolite (hereinafter referred to as "Y"), a physical adsorption-type drying agent, were mixed with the solution containing 48 wt % of aluminum oxide octylate (hereinafter referred to as "Z") (available from HOPE PHARMACEUTICAL CO., under the trade name "OLIPE AOO") illustrated by the chemical formula (7) which is an organometallic compound illustrated by the chemical formula (1) in the weight ratio of 2Z:1x:1Y and dispersed therein to prepare dispersion which was then applied to a sealing container in a dried atmosphere. Then, an organic EL device was prepared in the same manner as that of Example 6.

An accelerated life test was carried out on the emitting part of the organic EL device at a temperature of 85° C. and at relative humidity of 85%. Then, a microscopic examination was made on the emitting part of the organic EL device to confirm the growth of the dark spot. As a result, it was confirmed that while the initial diameter of the dark spot was 1 $\mu$m, it grew only up to 7 $\mu$m at the most after the elapse of 500 hours. Further, the generation and growth of the dark spot at the periphery of the emitting part of the organic EL device were not different from those of the central portion.

For reasons stated above, it is evident that the drying agent of the present invention is an excellent drying agent.

Comparative Example 1

Calcium oxide (CaO) as a drying agent was placed in the concave portion of a sealing cup. Then the sealing cup was placed opposite to the aforementioned organic EL laminate prepared in a manner similar to that of Example 1, and sealed by ultraviolet-curing type-epoxy resin to form an organic EL device.

An accelerated life test was carried out on the emitting part of the organic EL device at a temperature of 85° C. and at relative humidity of 85%. Then, a microscopic examination was made on the emitting part of the organic EL device to confirm the growth of the diameter of the dark spot. As a result, it was confirmed that while the initial diameter of the dark spot was 1 $\mu$m, it grew up to 11 $\mu$m after the elapse of 500 hours. Further, the number of the dark spot generated at the periphery of the organic EL device was larger than that at the central portion.

Comparative Example 2

The same procedures as those of Example 1 were repeated except that sealing was completed without a drying agent, and an organic EL device was prepared. The state of emission of the organic EL device was observed. Then, the organic EL device was put in an atmosphere of high temperature of 85° C. and high humidity of 85% to confirm water-capturing effect. After the elapse of 100 hours, the organic EL device was taken out of the atmosphere, and the state of emission of the organic EL device was observed. As a result, the growth of the dark spot was confirmed, and the area of emission was lowered to 60%, and emission could not be seen at all.

Example 16

In Example 16, a solution of the drying agent of the present invention in a nonaqueous solvent was sealed in the container of Example 1.

The same procedures as those of Example 1 were repeated except that: 48 wt % of aluminum oxide octylate (available from HOPE PHARMACEUTICAL CO. under the trade name "OLIPE AOO") illustrated by the chemical formula (7) which is an organometallic compound illustrated by the chemical formula (2) were dissolved in an inorganic non-aqueous solvent such as silicone etc., which is a dehydrated non-solvent or in an organic nonaqueous solvent to prepare a solution which was then sealed in a container in a dried atmosphere.

Then, an organic EL device was prepared in the same manner as that of Example 1.

In Example 16, while the above described aluminum oxide octylate was used in 48 wt %, the drying agent of the present invention may be changed in the range from 5 wt % to 60 wt %.

A microscopic examination was made on the emitting part of the organic EL device to confirm the growth of the dark spot at a temperature of 85° C. and at relative humidity of 85%. As a result, it was confirmed that while the initial diameter of the dark spot at the central portion was 1 $\mu$m, it grew only up to 7 $\mu$m at the most after the elapse of 500 hours. Further, the generation and growth of the dark spot at the periphery of the emitting part of the organic EL device were not different from those of the central portion.

Example 17

In Example 17, coloring powder was added to the drying agent of Example 1.

The same procedures as those of Example 1 were repeated except that: Coloring powder as colorant was dispersed in the solution containing 48 wt % of aluminum oxide octylate (available from HOPE PHARMACEUTICAL CO. under the trade name "OLIPE AOO") illustrated by the chemical formula (7) in 0.00001~10 wt % on the basis of the weight of the solution to prepare dispersion which was then applied to a sealing container in a dried atmosphere.

When the amount of the coloring powder is less than 0.00001 wt %, there is a case that color development is not sufficient. When it is more than 10 wt %, there is a case that the drying agent is dyed by the colorant before absorption of moisture, because the amount of the colorant is excessive.

As the above described colorant may be coloring matters such as color adding substances etc., dyes such as direct dyes, acid dyes, basic dyes, disperse dyes, reactive dyes, Izod dyes, etc., pigment, or cobalt chloride anhydride.

Thereafter, an accelerated life test was carried out on the emitting part of the organic EL device at a temperature of 85° C. and at relative humidity of 85%. Then, a microscopic examination was made on the emitting part of the organic EL device to confirm the growth of the dark spot. After the elapse of 100 hours, the organic EL device was taken out of an accelerated life test chamber, and the state of emission was observed. As a result, it was confirmed that the dark spot was hardly grown.

According to the present invention, an organic EL device provided with a polymer-type organic film such as polyvinyl carbazole (PVC) etc. instead of the above described organic films (4a, 4b, 4c) exhibits the same drying effect as that of the above described organic films.

According to the present invention, an organic EL device using a functional organic compound such as an organic solar cell etc., instead of the above described organic films (4a, 4b, 4c) exhibits the same drying effect as that of the above described organic films.

According to the present invention, when a "light-to-electron conversion device" or "light-to-light conversion device" having a laminate structure comprising "gold transparent electrode (cathode)/photocurrent amplifying film/organic EL film/gold transparent electrode (anode)" using an organic EL device technology is placed in a closed container provided with the drying agent of the present invention, it can be protected from degradation by moisture.

While the present invention is described particularly with reference to examples concerning an electronic part such as an organic EL device etc. using an organic materials, it should go without saying that the drying agent of the present invention can be used as a drying agent available in any other closed container.

According to the present invention, there is provided an organometallic compound having an excellent function as a drying agent.

According to the present invention, there is provided an organometallic compound having an excellent function as a drying agent which can be placed in a closed container.

According to the present invention, an organometallic compound having an excellent function as a drying agent can be applied on the surface of the closed container and dried to form a transparent dried film.

Since the drying agent of the present invention maintains solid state after absorption of moisture, it can be placed on the whole surface of the closed container.

According to the present invention, there is provided an excellent drying agent which can be used without distinction of environment and which can absorb moisture effectively at high humidity and at extremely low humidity.

According to the present invention, there is provided an excellent drying agent superior to a conventional one in that since it can form a water-capturing transparent film, an observation can be made clearly through the transparent water-capturing film.

What is claimed is:

1. A method for absorbing moisture from an environment, the method comprising:

placing in the environment a drying agent comprising an organometallic compound illustrated by the formula (1);

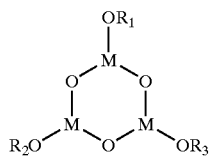

wherein, $R_1$, $R_2$ and $R_3$ are selected from the group consisting of alkyl group, aryl group, cycloalkyl group, heterocyclic group and acyl group having at least one carbon atom, and M is a trivalent metallic atom, whereby moisture is absorbed from the environment.

2. A method for absorbing moisture from an environment, the method comprising:

placing in the environment a drying agent comprising an organometallic compound illustrated by the formula (2);

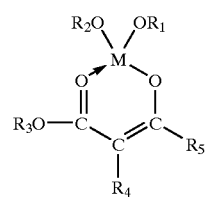

wherein, $R_1$, $R_2$, $R_3$, $R_4$ and $R_5$ are selected from the group consisting of alkyl group, aryl group, cycloalkyl group, heterocyclic group and acyl group having at least one carbon atom, and M is a trivalent metallic atom, whereby moisture is absorbed from the environment.

3. A method for absorbing moisture from an environment, the method comprising:

placing in the environment a drying agent comprising an organometallic compound illustrated by the formula (3);

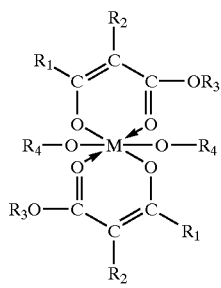

wherein, $R_1$, $R_2$, $R_3$ and $R_4$ are selected from the group consisting of alkyl group, aryl group, cycloalkyl group, heterocyclic group and acyl group having at least one carbon atom, and M is a quadrivalent metallic atom, whereby moisture is absorbed from the environment.

4. A method as defined in claim 1, wherein the drying agent further comprises an additional drying agent.

5. A method as defined in claim 4, wherein said additional drying agent is a physical adsorption-type drying agent.

6. A method as defined in claim 4, wherein said additional drying agent is a chemisorption-type drying agent.

7. A method as defined in claim 4, wherein said drying agent is mixed with a chemisorption-type drying agent and a physical adsorption-type drying agent.

8. A method as defined in claim 1, wherein said drying agent is placed on an inner surface of a sealed container.

9. A method as defined in claim 1, wherein said drying agent is dispersed in a nonaqueous solvent in a closed container.

10. A method as defined in claim 1, wherein the drying agent further comprises a colorant.

11. A method as defined in claim 2, wherein the drying agent further comprises an additional drying agent.

12. A method as defined in claim 11, wherein said additional drying agent is a physical adsorption-type drying agent.

13. A method as defined in claim 11, wherein said additional drying agent is a chemisorption-type drying agent.

14. A method as defined in claim 11, wherein said drying agent is mixed with a chemisorption-type drying agent and a physical adsorption-type drying agent.

15. A method as defined in claim 2, wherein said drying agent is dispersed in a nonaqueous solvent in a closed container.

16. A method as defined in claim 2, wherein the drying agent further comprises colorant.

17. A method as defined in claim 3, wherein the drying agent further comprises an additional drying agent.

18. A method as defined in claim 17, wherein said additional drying agent is a physical adsorption-type drying agent.

19. A method as defined in claim 17, wherein said additional drying agent is a chemisorption-type drying agent.

20. A method as defined in claim 17, wherein said drying agent is mixed with a chemisorption-type drying agent and a physical adsorption-type drying agent.

21. A method as defined in claim 3, wherein said drying agent is dispersed in a nonaqueous solvent in a closed container.

22. A method as defined in claim 3, wherein the drying agent further comprises a colorant.

* * * * *